(12) United States Patent
Tappehorn et al.

(10) Patent No.: US 11,660,417 B2
(45) Date of Patent: May 30, 2023

(54) NONRETURN VALVE FOR A COMPACT VENTILATION SYSTEM AS WELL AS COMPACT VENTILATION SYSTEM

(71) Applicant: Drägerwerk AG & Co. KGaA, Lübeck (DE)

(72) Inventors: Ludger Tappehorn, Lübeck (DE); Klaus Abraham, Lübeck (DE); Thorsten Dunkel, Fahrenkrug (DE); Andreas Junk, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1231 days.

(21) Appl. No.: 16/193,290

(22) Filed: Nov. 16, 2018

(65) Prior Publication Data

US 2019/0151602 A1 May 23, 2019

(30) Foreign Application Priority Data

Nov. 17, 2017 (DE) ...................... 20 2017 005 964.9

(51) Int. Cl.
*A61M 16/20* (2006.01)
*F16K 15/14* (2006.01)
*A61M 16/00* (2006.01)
*A62B 18/10* (2006.01)

(52) U.S. Cl.
CPC .......... *A61M 16/208* (2013.01); *A61M 16/00* (2013.01); *A61M 16/207* (2014.02); *F16K 15/144* (2013.01); *F16K 15/148* (2013.01); *A62B 18/10* (2013.01)

(58) Field of Classification Search
CPC ............... A61M 16/208; A61M 16/207; F16K 15/144; F16K 15/148; A62B 18/10
See application file for complete search history.

(56) References Cited

U.S. PATENT DOCUMENTS

| | | | |
|---|---|---|---|
| 3,527,242 A | 9/1970 | Ansite | |
| 3,990,439 A * | 11/1976 | Klinger | A62B 18/10 137/854 |
| 2010/0024824 A1 * | 2/2010 | Chalvignac | A61M 16/209 128/205.24 |
| 2011/0232640 A1 | 9/2011 | Van Dijk et al. | |
| 2013/0312757 A1 | 11/2013 | Cragg et al. | |

FOREIGN PATENT DOCUMENTS

| | | |
|---|---|---|
| GB | 748363 A | 5/1956 |
| WO | 2015054747 A1 | 4/2015 |

* cited by examiner

*Primary Examiner* — Margaret M Luarca
(74) *Attorney, Agent, or Firm* — McGlew and Tuttle, P.C.

(57) ABSTRACT

A nonreturn valve (10) for a compact ventilation system (100), includes a recoil membrane (20) and a holding element (40) for holding the recoil membrane (20) and for fastening the nonreturn valve (10) at a flow duct (110) of the compact ventilation system (100). The recoil membrane (20) has at least one mechanical stabilizing section (22) for cooperating with at least one mechanical counter-stabilizing section (42) of the holding element (40) or of the flow duct (110) of the compact ventilation system (100). At least one opening section (24) is provided for the defined movement of the recoil membrane (20) during the opening of the nonreturn valve (10) and a holding section (26) is provided for holding the recoil membrane (20) at a counter-holding section (46) of the holding element (40). A compact ventilation system (100) is provided with such a nonreturn valve (10).

20 Claims, 10 Drawing Sheets

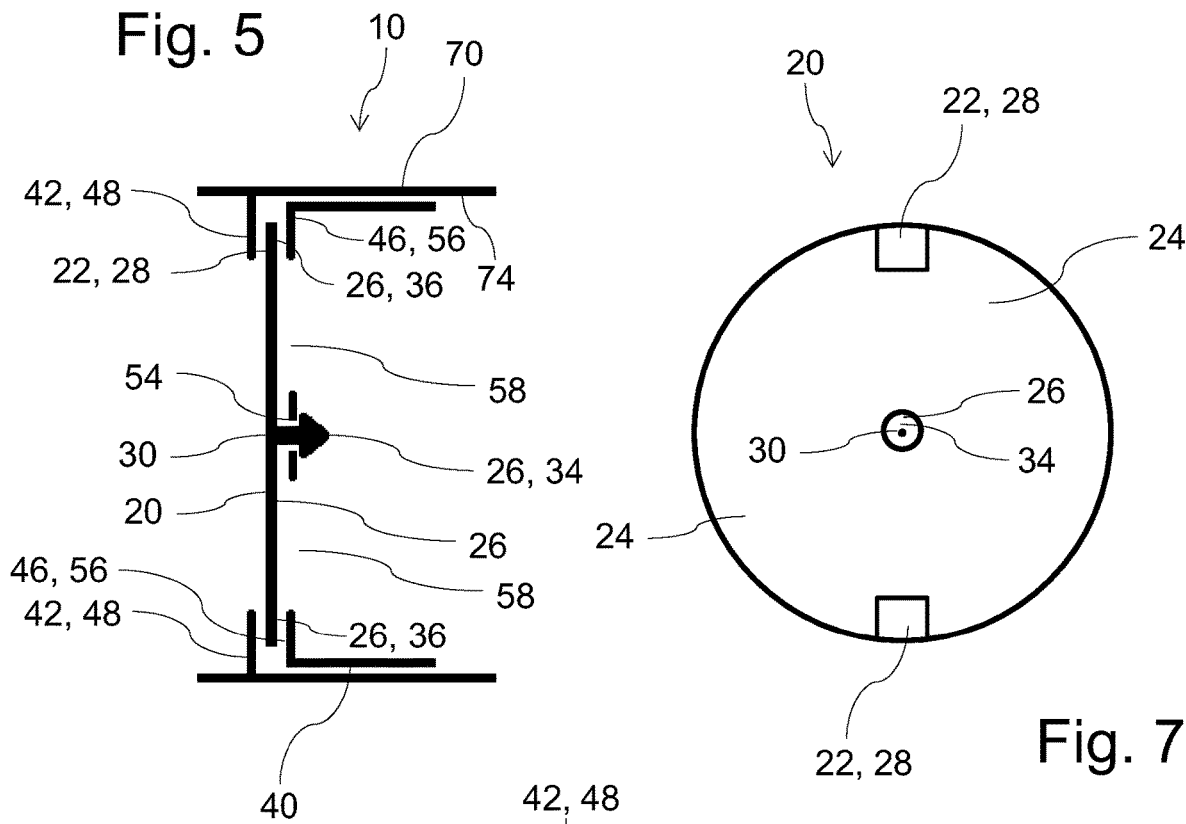
Fig. 5
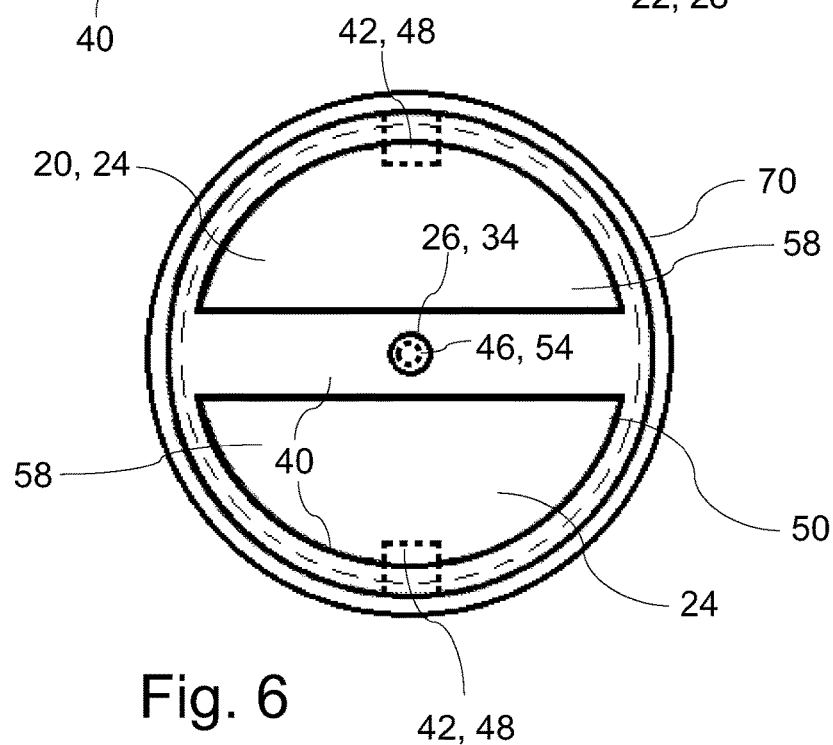
Fig. 6
Fig. 7

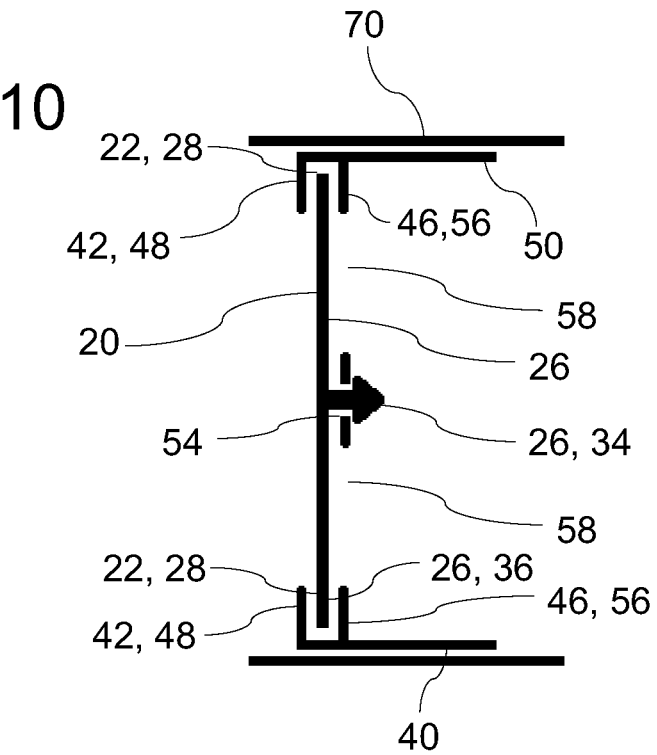
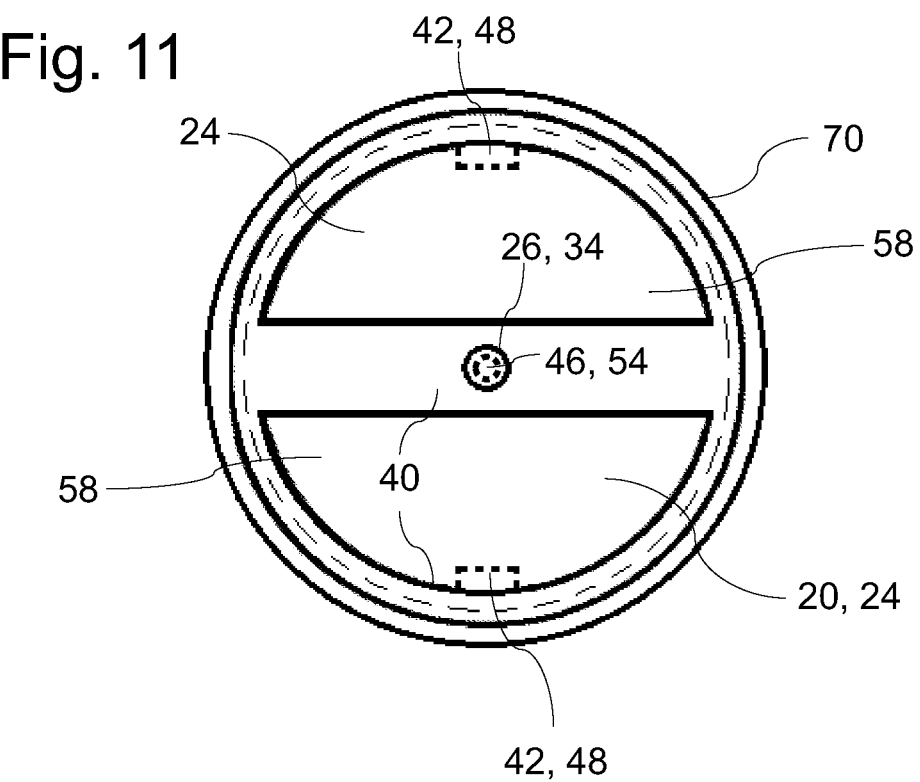

Fig. 12
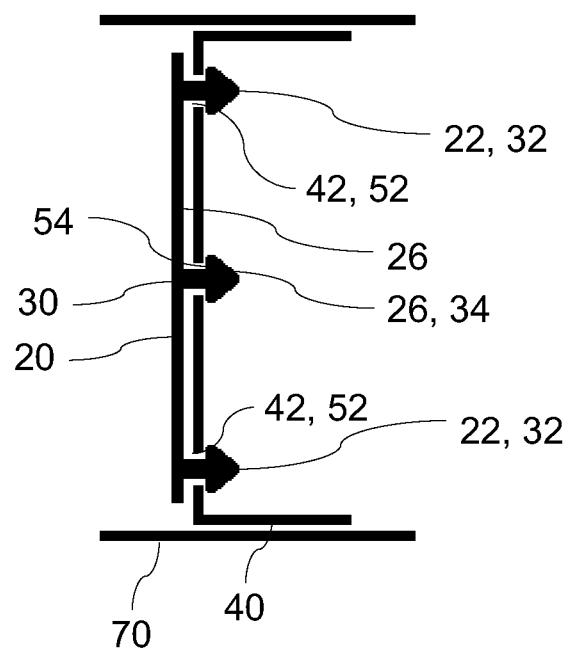
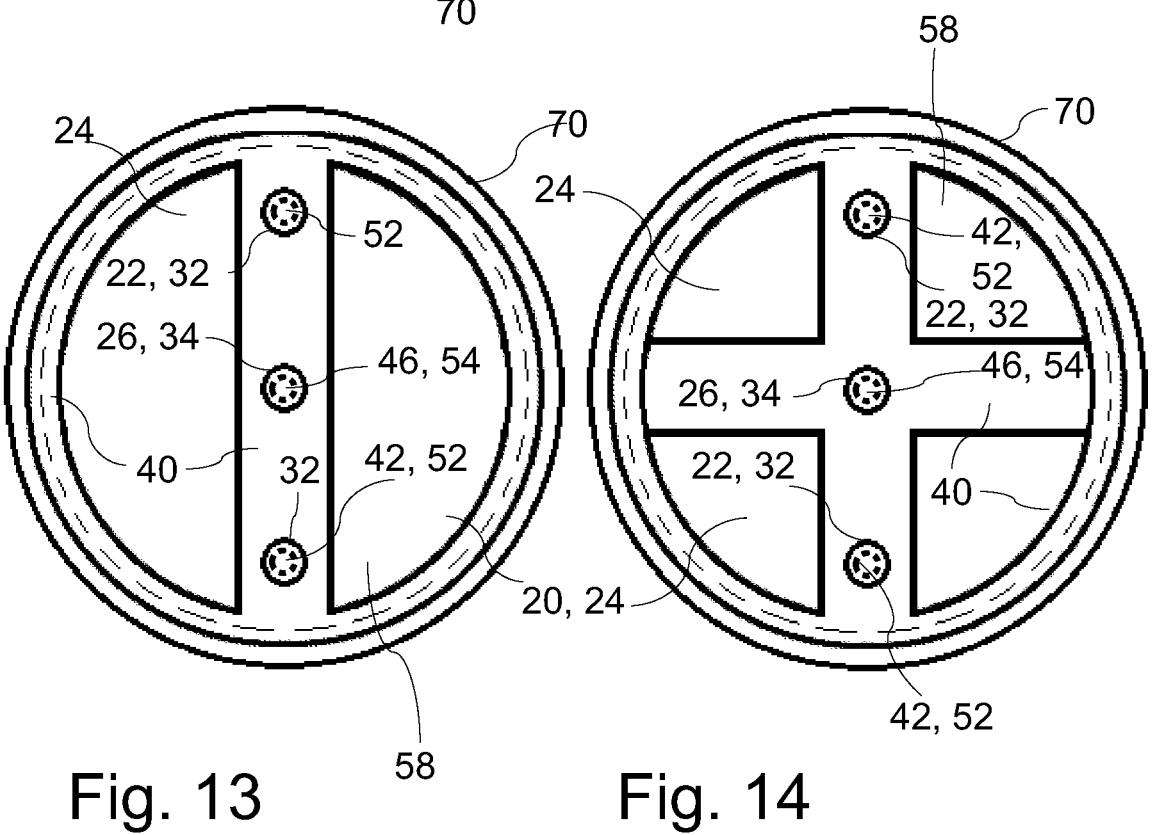
Fig. 13
Fig. 14

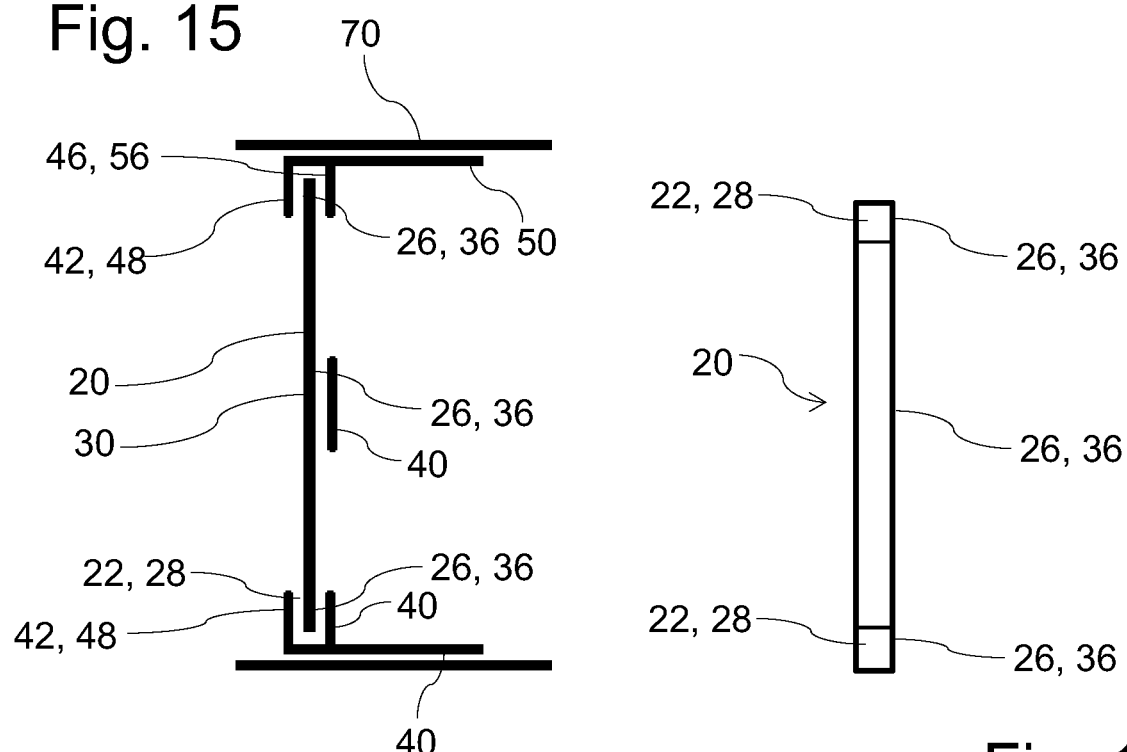
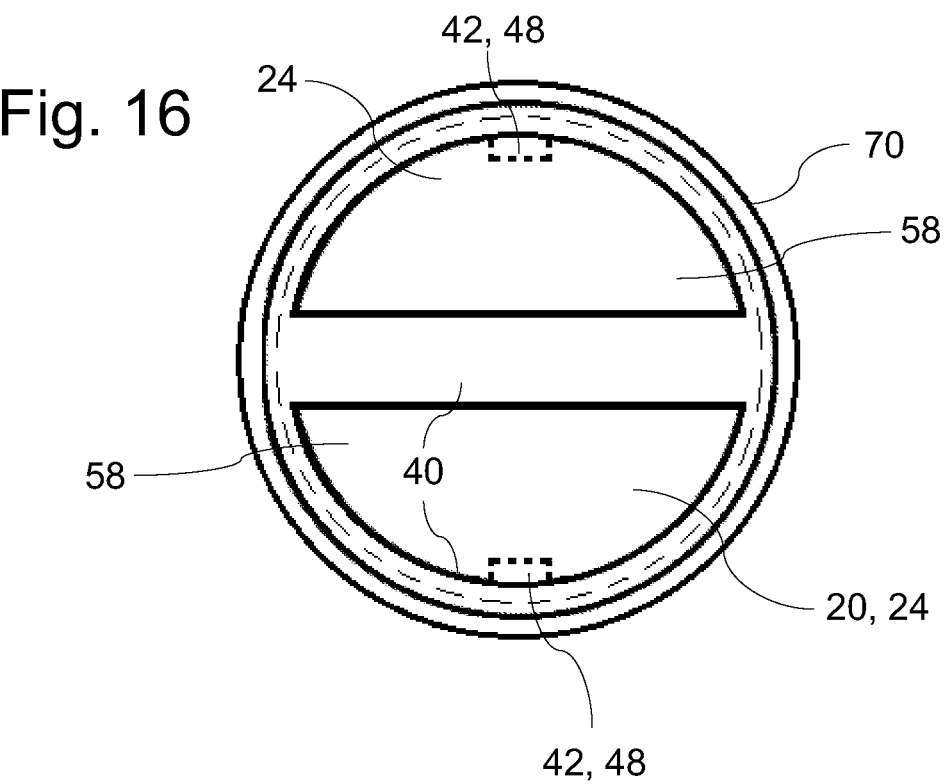

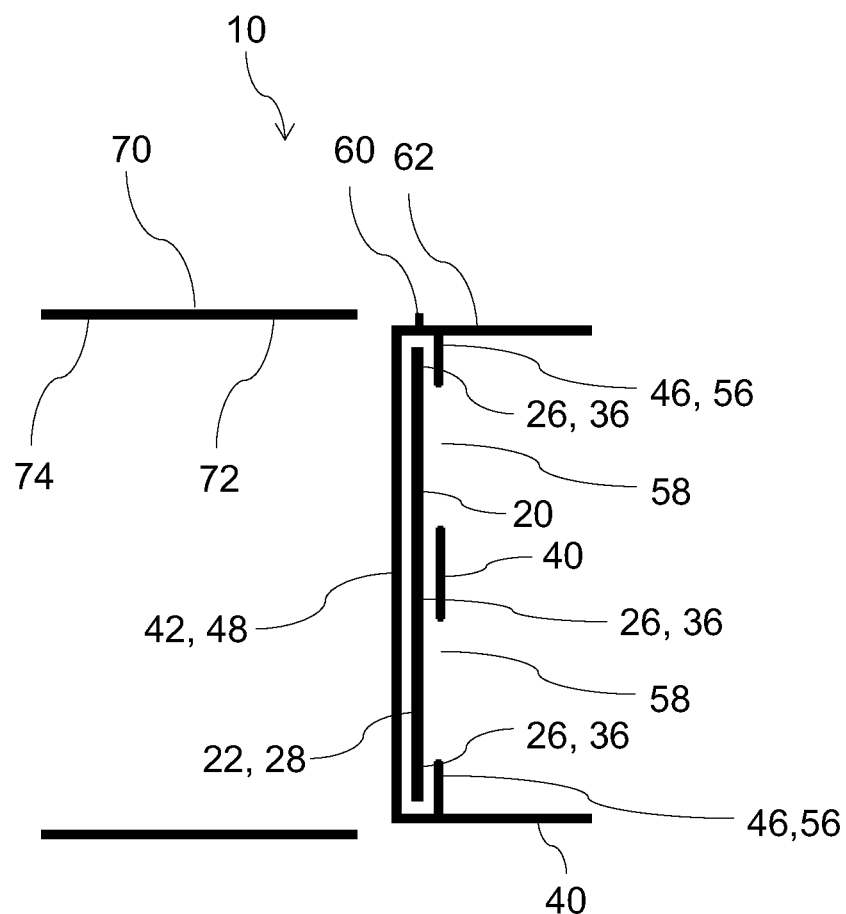
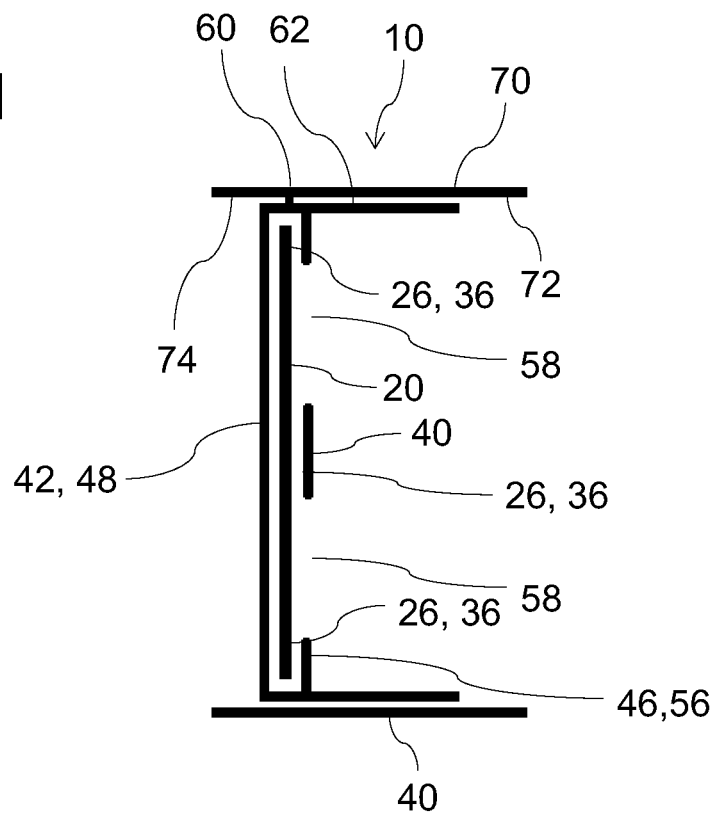

US 11,660,417 B2

NONRETURN VALVE FOR A COMPACT VENTILATION SYSTEM AS WELL AS COMPACT VENTILATION SYSTEM

CROSS REFERENCE TO RELATED APPLICATIONS

This application claims the benefit of priority under 35 U.S.C. § 119 of German Application 20 2017 005 964.9, filed Nov. 17, 2017, the entire contents of which are incorporated herein by reference.

TECHNICAL FIELD

The present invention pertains to a nonreturn valve for a compact ventilation system (also known as a compact respiration system), with a recoil membrane and with a holding element for holding the recoil membrane and for fastening the nonreturn valve at a flow duct of the compact ventilation system. The present invention further pertains to a compact ventilation system, having a fan, a tube as well as a flow duct for passing through breathing air to a patient, the flow duct having a first opening for connecting the fan, a second opening for connecting the tube, a volume flow meter, an exhalation valve as well as a nonreturn valve with a recoil membrane and with a holding element for holding the recoil membrane and for fastening the nonreturn valve at a flow duct of the compact ventilation system.

BACKGROUND

Compact ventilation systems are used especially for mobile applications in emergency medicine or in the primary care of emergency patients. Thus, compact ventilation systems are used, for example, during transportation in rescue vehicles or in helicopters. Patients can thus be ventilated with compact ventilation systems during transfers from one hospital to another hospital.

Compact ventilation systems have a fan, which is used to deliver breathing air to a patient. The breathing air provided by the fan passes through a flow duct to a tube, which the patient places over his/her nose or his/her mouth. To send both breathing air to the patient, the so-called inhalation, and to send the exhaled air away from the patient, the so-called exhalation, through the compact ventilation system, these compact ventilation systems have an exhalation valve as well as a recoil membrane. Such systems further have volume flow meters or flow sensors, which monitor the breathing air and the exhaled air during the ventilation. This means that especially compact ventilation systems, especially for ventilation during the transportation of the patient, have compact tube systems. These tube systems require functional elements, such as an exhalation valve, a nonreturn valve, to prevent the exhaled air from being returned back to the fan, as well as an element for measuring the breathing air flow. The volume flow meter or flow sensor is ideally arranged as close to the patient as possible, especially in the proximity of the tube, so that both the inhalation (breathing air to the patient) and the exhalation (exhaled air away from the patient) can be monitored. The volume flow meter shall be very robust due to the very different and extreme ambient conditions for the use of these compact ventilation systems. Indirect volume flow measurement based on the pressure difference, in which case the pressure difference sensor proper is accommodated in the compact ventilation system, is frequently used for this reason. In particular, a volume flow meter is used, which is arranged close to the patient, to linearize the flow/pressure difference characteristic. The ventilation branches inhalation and exhalation are defined by the arrangement of the functional elements within the compact ventilation system. The nonreturn valve with its recoil membrane, which membrane opens during the inhalation, so that breathing air provided by the fan can be delivered through the flow duct of the compact ventilation system in the direction of the patient, is arranged downstream of the fan in the flow duct of a compact ventilation system. The exhalation valve is closed during the inhalation, so that the breathing air passed through the recoil membrane is sent past the exhalation valve and the volume flow meter and is sent to the tube of the flow duct. The exhalation valve is located between the recoil membrane and the volume flow meter and ensures that air exhaled during the exhalation can escape from the exhalation valve into the surrounding area. The recoil membrane is closed during the exhalation for this to happen, i.e., this membrane prevents exhaled air from being sent back to the fan.

Air flows out of the fan in the direction of the patient during the phase of inhalation. The membrane of the exhalation valve is lowered onto a so-called exhalation opening by a control line of the exhalation valve and the exhalation opening is thus closed. It is ensured by the area ratios and the pressures above and below the membrane that the exhalation opening remains closed during the phase of inhalation. The recoil membrane opens the path of the breathing air in the direction of the patient. The flow takes place through the flow duct in the exhalation valve. The breathing air subsequently flows through the volume flow meter and bends in the process a membrane or a wire, which membrane or wire is installed in the volume flow meter of the compact ventilation system to linearize the pressure difference.

The exhaled air flows out of the patient's lungs during the phase of exhalation via the tube into the volume flow meter, and the membrane or the wire is bent in the process in the opposite direction compared with the phase of inhalation. The recoil membrane of the nonreturn valve is closed by the airway pressure. The pressure to the control line of the exhalation valve is reduced, so that the membrane is lifted off from the exhalation opening and the exhaled air can flow into the surrounding area. The control pressure may be varied at the end of the exhalation via the control line in order to generate the end-aspiratory pressure—positive end-expiratory pressure (PEEP).

The drawback of such compact ventilation systems is that vibrations developing especially during the phase of exhalation have a direct effect on the volume flow measurement of the volume flow meter due to the uncontrolled opening of the recoil membrane. This effect becomes especially unforeseeable because the recoil membranes of prior-art nonreturn valves do not always open in the same manner. In currently known nonreturn valves of compact ventilation systems, a flexible membrane is fastened, centered in the flow duct, at a centrally positioned holding element. Centered in this case means that the usually circular membrane is fixed in the area of its center at the holding element. The breathing air provided by the fan flows in the direction of the recoil membrane during the phase of inhalation and opens this at times at the top, at times on the side, at times at the bottom, always differently depending on the different incoming flows of the breathing air. The uncontrolled opening of the recoil membrane during the phase of inhalation leads to different swirls in the breathing air flow in the flow duct of the compact ventilation system, which markedly affects, especially impairs, the accuracy of measurement of the volume flow meter. However, the volume flow meter depends on a defined incoming flow for carrying out accurate measurements. Due to the central suspension of the recoil membrane in the flow duct of the compact ventilation system, the accuracy of the volume flow measurement can only be predicted very poorly.

SUMMARY

An object of the present invention is to at least partially eliminate the above-described drawbacks in a compact ventilation system. An object of the present invention is, in particular, to provide a compact ventilation system that makes it possible that the flow arrives in a controlled manner at the volume flow meter in all cases, so that the measurement accuracy of the volume flow meter becomes predictable. The recoil membrane shall open in a defined manner and close reliably during the exhalation. Further, the position dependence of the recoil membrane shall be reduced.

According to a first aspect, the object is accomplished by a nonreturn valve for a compact ventilation system, with a recoil membrane and with a holding element for holding the recoil membrane and for fastening the nonreturn valve to a flow duct of the compact ventilation system. The nonreturn valve according to the present invention is characterized here such that the recoil membrane has at least one mechanical stabilizing section for cooperating with at least one mechanical counter-stabilizing section of the holding element or of the flow duct of the compact ventilation system, at least one opening section for the defined movement of the recoil membrane during the opening of the nonreturn valve and a holding section for holding the recoil membrane at a counter-holding section of the holding element.

It can be guaranteed by such a nonreturn valve that the recoil membrane opens in a defined manner during the phase of inhalation and closes reliably during the phase of exhalation. Due to the recoil membrane being divided into different sections, which have different technical functions, the breathing air delivered by the fan can always be sent through the nonreturn valve in the same manner or in approximately the same manner, so that the subsequent delivery of the breathing air in the flow duct of a compact ventilation system in the direction of the volume flow meter of the compact ventilation system, in which the nonreturn valve is used, always takes place in the same manner or in approximately the same manner. It is ensured thereby that the accuracy of the volume flow measurement is optimized and is especially predictable.

The at least one mechanical stabilizing section is used to cooperate with at least one mechanical counter-stabilizing section of the holding element or of the flow duct of the compact ventilation system. Cooperation means, in the sense of the present invention, that the at least one mechanical stabilizing section of the recoil membrane is held at the at least one mechanical counter-stabilizing section of the holding element of the nonreturn valve or of the flow duct of the compact ventilation system, so that the recoil membrane is not moved in the area of the at least one mechanical stabilizing section during the opening of the recoil membrane, but remains firmly fixed at the holding element. In other words, the recoil membrane is held in the area of the at least one mechanical stabilizing section at the at least one mechanical counter-stabilizing section, so that the recoil membrane remains arranged immovably in the nonreturn valve in the area of the at least one mechanical stabilizing section both during the phase of inhalation and during the phase of exhalation. The recoil membrane further has a holding section for holding the recoil membrane at a counter-holding section of the holding element. The holding section is likewise used for the defined arrangement of the recoil membrane within the nonreturn valve, i.e., the holding section of the nonreturn valve is used especially for the defined positioning and holding of the recoil membrane at the holding element of the nonreturn valve during the phase of exhalation. The holding section of the recoil membrane ensures that the recoil membrane is pressed against the holding element of the nonreturn valve in a defined manner during the phase of exhalation and it thereby closes the nonreturn valve, so that air exhaled by the patient cannot flow through the nonreturn valve in the direction of the fan. In order for breathing air, which is provided by the fan, to be able to flow through the nonreturn valve during the phase of inhalation, the recoil membrane has at least one opening section. The at least one opening section is used for the defined movement of the recoil membrane during the opening of the nonreturn valve, i.e., the at least one opening section is lifted off from the holding element during the arrival of the flow of breathing air provided by the fan and it thus makes it possible for the breathing air to be sent through the nonreturn valve in the direction of the patient. Due to the fact that the at least one mechanical stabilizing section of the recoil membrane is arranged firmly at the at least one mechanical counter-stabilizing section of the holding element or of the flow duct of the compact ventilation system, only the at least one opening section moves away from the holding element during the flow of the breathing air during the phase of inhalation. It is ensured thereby that the flow of breathing air through the nonreturn valve can always be the same or approximately the same. The consequence of this is, in turn, that there is a defined incoming flow of the breathing air through the flow duct of the compact ventilation system to the volume flow meter of the compact ventilation system in order to make the measurement accuracy of the volume flow meter predictable. Such a nonreturn valve for a compact ventilation system makes possible, furthermore, a defined opening of the recoil membrane during the phase of inhalation and reliable closing of the recoil membrane during the phase of exhalation. The position dependence of the nonreturn valve within the flow duct of a compact ventilation system is also reduced due to the different sections of the recoil membrane and the defined arrangement of the recoil membrane at the holding element of the nonreturn valve, which is associated therewith, i.e., the nonreturn valve does not have to be arranged in a very specific position within the flow duct of the compact ventilation system, but it may be arranged in a broader range in front of the fan.

According to a preferred variant of the present invention, provisions may be made in a nonreturn valve for the holding element to have a cylindrical, especially disk-shaped, ring element-type or basket element-type configuration and to have passages for the flow of breathing air. Due to the cylindrical configuration of the holding element, the latter can be arranged within the flow duct of a compact ventilation system in a simply positive-locking manner. The longitudinal axis of the flow duct preferably corresponds here to the longitudinal axis of the holding element. Optimal sealing can be guaranteed between the outer side of the holding element and the flow duct by means of seals on the outer jacket surface of the cylindrical holding element or on the inner jacket surface of the cylindrical flow duct. A defined positioning of the cylindrical holding element within the flow duct can be ensured in different manners. For example, the flow duct may have a configuration tapering beginning from a certain area, so that the cylindrical holding element can be inserted into the flow duct up to the taper, but it is locked there because of the taper. A disk-shaped or ring element-type configuration of the holding element makes possible a very compact configuration of the nonreturn valve, i.e., with small outer, especially axial dimensions. Passages are provided for the flow of breathing air in the disk-shaped holding element and in the ring element-type holding element. Thus, the holding element may be, for example, a perforated disk. Further, a ring element-type holding element may be provided with webs, which act as counter-holding sections. A holding element, which is configured as a basket element, has, in principle, a disk-shaped or ring element-type bottom, on the outer side of which a hollow cylindrical section adjoins. Such a basket element can be inserted into the flow duct of a compact ventilation system and positioned in the corresponding position in an especially simple manner. The basket element also has passages in the area of its bottom for the flow of breathing air through the nonreturn valve.

According to another preferred variant of the present invention, provisions may be made in a nonreturn valve for the mechanical stabilizing section to be a segment of the recoil membrane or two segments of the recoil membrane, which are located opposite each other in relation to the center of the recoil membrane, and for the counter-stabilizing section of the holding element to be at least one counter-segment of the holding element or of the flow duct of the compact ventilation system, wherein the segment/segments of the recoil membrane is/are in contact with the at least one counter-segment of the holding element in a non-positive and/or positive-locking manner. For example, the segment of the recoil membrane may be a straight strip extending in the recoil membrane through the center of the recoil membrane. As an alternative, the mechanical stabilizing section may be formed by two segments of the recoil membrane, which are mirror-symmetrical to each other about the center of the recoil membrane. For example, one segment of the recoil membrane may be provided on a first edge of the recoil membrane and the other segment in an edge area of the recoil membrane, which is arranged offset by 180° in relation to the first edge of the recoil membrane. The mechanical stabilizing section of the recoil membrane, which section is formed by one segment or two segments, is used to form a non-positive and/or positive-locking connection with the at least one mechanical counter-stabilizing section of the holding element or of the flow duct of the compact ventilation system, which counter-stabilizing section is configured as a counter-segment. The at least one mechanical stabilizing section or the segment/segments may have a reinforced configuration. For example, the recoil membrane may be made of a more solid, more dimensionally stable material in the area of the mechanical stabilizing sections than the recoil membrane in the area of the at least one opening section. It can be ensured hereby that the recoil membrane is not destroyed or damaged when the functional connection is established between the at least one mechanical stabilizing section and the at least one mechanical counter-stabilizing section of the holding element or of the flow duct. The recoil membrane is locked in a nonreturn valve of such a configuration preferably in the area of the at least one mechanical stabilizing section between the holding element of the nonreturn valve and the at least one mechanical counter-stabilizing section of the flow duct of a compact ventilation system. It is ensured by the locking effect that the recoil membrane remains firmly arranged within the nonreturn valve in the area of the at least one mechanical stabilizing section during the incoming flow of breathing air during the phase of inhalation. The recoil membrane can only move in the area of the at least one opening section during the phase of inhalation, so that it is ensured that the opening of the recoil membrane is always the same and that consequently there is a defined flow of breathing air during the phase of inhalation.

Provisions may further be made in an advantageous nonreturn valve for the mechanical stabilizing section to be at least one suspension element projecting from the recoil membrane, which suspension element is locked in at least one mechanical counter-suspension element of the holding element, which suspension element is configured as a recess. In other words, the recoil membrane may have one or two suspension elements, which are preferably arranged at the edge. The at least one projecting suspension element preferably has a mushroom- or hammer-shaped configuration, so that it is locked on the rear side of the holding element after being passed through the mechanical counter-suspension element configured as a recess. It is guaranteed by this at least one locking connection that the recoil membrane remains firmly fixed on the holding element by the at least one mechanical stabilizing section during the phase of inhalation. The recoil membrane preferably has two mechanical stabilizing sections of such a configuration, which project from the recoil membrane offset in relation to each other by 180° in the vicinity of the edge area of the recoil membrane. It is ensured in case of such a configuration of the nonreturn valve that only the at least one opening section of the recoil membrane can move in a defined manner in the direction of the recoil membrane during the flow of breathing air during the phase of inhalation and thus it ensures a defined flow of breathing air through the nonreturn valve.

According to another preferred variant of the present invention, provisions may be made in a nonreturn valve for the mechanical stabilizing section of the recoil membrane to be a web-type thickening (web thickening) in the recoil membrane itself. This web-type thickening or reinforcing rib of the recoil membrane is used to impart a dimensionally stable configuration to the recoil membrane in the mechanical stabilizing section and to enable the web-type thickening not to change its position in relation to the holding element during the arrival of the flow of breathing air to the nonreturn valve, so that only the at least one opening section is moved by the nonreturn valve in a defined manner during the flow of breathing air through the nonreturn valve. This in turn ensures a defined incoming flow to the volume flow meter arranged downstream in the flow duct of a compact ventilation system, so that the measurement accuracy of the volume flow meter is predictable at a very high accuracy. The web-type thickening in the recoil membrane may be brought about by a thickening of the material. In addition, reinforcements, such as a grid structure made of metal, may be provided in the web-type thickening.

According to another preferred variant of the present invention, provisions may be made in a nonreturn valve for the holding section of the recoil membrane to be a suspension element projecting from the recoil membrane, which suspension element is locked into a counter-suspension element of the holding element, which counter-suspension element is configured as a recess, or for the holding section to be a contact surface on one side of the recoil membrane, which is configured to come into clamping contact with a counter-holding section of the holding element, which counter-holding section is configured as a counter-contact surface. The holding section of the recoil membrane has the function of holding the recoil membrane in a defined position at the holding element. This can be achieved, on the one hand, by a contact surface of the recoil membrane being pressed or clamped onto a counter-contact surface of the holding element and holding hereby the recoil membrane in a certain position at the holding element. The contact surface is arranged on the side of the recoil membrane that is directed in the direction of the fan of the compact ventilation system on installation of the nonreturn valve in a compact ventilation system. As an alternative or in addition, the holding section of the recoil membrane may be configured as a suspension element, which projects from the recoil membrane and is locked into a counter-suspension element of the holding element, which counter-suspension element is configured as a recess. The suspension element may be configured as a locking hook, preferably with a mushroom- or hammer-shaped configuration. The projecting suspension element is preferably arranged at the recoil membrane in the area of the center of said recoil membrane. In particular, the projecting suspension element is arranged at right angles to the recoil membrane. The holding section configured as a projecting suspension element and the mechanical stabilizing section configured as a projecting suspension element may be identical in terms of shape and size. In conjunction with the at least one mechanical stabilizing section of the recoil membrane, the holding section of the recoil membrane is used to fasten the recoil membrane in a defined manner within the nonreturn valve, especially at the holding element of the nonreturn valve. The projecting suspension elements of the at least one mechanical stabilizing section and of the holding section can thus be arranged along a straight line passing through the center of the recoil membrane, so that the recoil membrane is firmly fixed at the holding element of the nonreturn valve in the area of this straight line. Only the opening sections of the recoil membrane, which are arranged laterally from the straight line, can be lifted off from the holding element and thus guarantee a defined flow of breathing air through the nonreturn valve during the incoming flow of breathing air during the phase of inhalation.

A nonreturn valve in which the recoil membrane has two opening sections arranged on two opposite sides of the recoil membrane in relation to the center of the recoil membrane is correspondingly advantageous. The recoil membrane is firmly anchored in the case of such a nonreturn valve along a straight line passing through the center of the recoil membrane at the holding element. Only the opening sections located to the right and left of the anchoring remain movable and can open the nonreturn valve during the phase of inhalation and close the nonreturn valve again during the phase of exhalation. The two opening sections are arranged in a wing-shaped manner to the left and right of a straight area, at which the at least one mechanical stabilizing section and the holding section of the recoil membrane are located.

Further, provisions may be made in a nonreturn valve for the counter-segment of the holding element to be configured as a longitudinal web or as two hooks projecting radially from the jacket surface of the cylindrical holding element. In other words, the counter-segment of the holding element, which forms the counter-stabilizing section of the holding element, may be a longitudinal web, which extends from one side of the inner jacket surface of the cylindrical holding element through the longitudinal axis of the nonreturn valve to an opposite, second side of the inner jacket surface of the cylindrical holding element. The longitudinal web extends parallel to the recoil membrane when the latter is sealingly in contact with the holding element during the phase of exhalation. It is ensured thereby that the recoil membrane is locked between the counter-holding section of the holding element and the counter-segment or counter-stabilizing section of the holding element, which counter-segment or counter-stabilizing section is configured as a longitudinal web. The opening sections of the recoil membrane, which are arranged to the left and right of the longitudinal web, are bent during the incoming flow of breathing air, while the recoil membrane is held in the area of its mechanical stabilizing section at the mechanical counter-stabilizing section configured as a longitudinal web. As an alternative to this, the counter-segment of the holding element may be configured as two radial hooks or projections projecting from the jacket surface of the cylindrical holding element. A likewise defined fixation of the recoil membrane at the holding element can be achieved hereby in conjunction with a holding section of the recoil membrane, which holding section is configured as a projecting suspension element. The recoil membrane has two movable opening sections here as well, which guarantee a defined flow through the nonreturn valve during the phase of inhalation.

Furthermore, a nonreturn valve, in which the nonreturn valve has a tube element, and in which the holding element is fastened to the inner jacket surface of the tube element in a non-positive and/or positive-locking manner, is preferred. This means that the nonreturn valve may have a tube element itself and can thus correspondingly become simply a part of a flow duct of a compact ventilation system. A nonreturn valve having such a configuration can be mounted in an especially simple manner, but it can also be removed in a compact ventilation system, so that it can be ensured that a reliably functioning nonreturn valve is always used in the compact ventilation system. Provisions may preferably be made in case of the tube element that this has at least one mechanical counter-stabilizing section. In other words, the tube element may have as the mechanical counter-stabilizing section a web, which extends from an inner jacket surface of the tube element to the opposite inner jacket surface of the tube element and which is used to fix the recoil membrane between it and the holding element of the nonreturn valve. As an alternative to this, two hooks or projections may be provided, which project radially on opposite sides of the inner jacket surface of the tube element, and which are used as mechanical stabilizing sections. The recoil membrane can be fastened in a defined manner within the nonreturn valve and guarantee a defined opening of the opening sections of the recoil membrane during the phase of inhalation in such a configuration as well.

The tube element of the nonreturn valve may have a sliding block guide in its inner jacket surface, in which a corresponding bolt can be guided in a lockable manner on the outer jacket surface of the holding element of the nonreturn valve. It can be guaranteed thereby that when the holding element is mounted in the tube element of the nonreturn valve, the nonreturn valve can be guided specifically to a very specific position, which ensures an optimal flow of breathing air through the nonreturn valve upon a later installation of the nonreturn valve.

Provisions may especially preferably be made in a nonreturn valve for the counter-holding section of the holding element to be a counter-suspension element, which projects from the holding element and which is locked into a holding section of the recoil membrane, which holding section is configured as a recess, the counter-suspension element having a width that is greater than the holding section configured as a recess, and especially having a size equaling at least twice the size of the holding section configured as a recess. The counter-suspension element preferably has a radial extension relative to the longitudinal axis of the holding section configured as a recess that corresponds to at least 2 to 3 times the diameter of the holding section configured as a recess. A nonreturn valve having such a configuration makes possible a defined retention of the recoil membrane during the outflow of breathing air or during a flow of breathing air during the phase of inhalation. The counter-suspension element preferably has an oblong shape, especially an oval-oblong shape. The counter-suspension element locks the recoil membrane at the holding element and ensures that only the opening sections of the recoil membrane that are located to the left and right of the counter-suspension element can be moved.

According to a second aspect of the present invention, the object is accomplished by a compact ventilation system, having a fan, a tube as well as a flow duct for passing through breathing air to a patient, wherein the flow duct has a first opening for connecting the fan, a second opening for connecting the tube, a volume flow meter, an exhalation valve as well as a nonreturn valve with a recoil membrane and with a holding element for holding the recoil membrane and for fastening the nonreturn valve on a flow duct of the compact ventilation system. According to the present invention, such a compact ventilation system has a nonreturn valve, which is configured according to the first aspect of the present invention. Such a compact ventilation system has the same advantages that were already described in detail in connection with the nonreturn valve according to the first aspect of the present invention. In particular, it can be guaranteed in the compact ventilation system based on the nonreturn valve according to the present invention that the flow of the breathing air during the phase of inhalation has repeated reproducibility. In other words, it can be guaranteed based on the special fastening of the recoil membrane within the nonreturn valve that the recoil membrane always opens in the same manner during the phase of inhalation, so that a uniform breathing air flow, which is provided by the fan of the compact ventilation system, can always be sent through the flow duct of the compact ventilation system. In particular, it can be ensured that the swirls of the breathing air having flown through are always the same or approximately the same. The combination of controlled opening of the recoil membrane, of a defined orientation of the recoil membrane or of the nonreturn valve in relation to the volume flow meter, and of a defined flow duct in the exhalation valve, which is arranged between the volume flow meter and the nonreturn valve in the flow duct of the compact ventilation system, ensures a predictable incoming flow of breathing air to the volume flow meter. The recoil membrane is lifted off from the holding element, especially from the disk-shaped, ring element-shaped or basket-shaped holding element, during the phase of inhalation only with the opening section or the opening sections of the recoil membrane, correspondingly releasing the flow of the breathing air through the flow duct in the direction of the volume flow meter.

Provisions may preferably be made in a compact ventilation system for the flow duct to have at least one mechanical counter-stabilizing section for cooperating with the at least one mechanical stabilizing section of the recoil membrane. In other words, the at least one mechanical counter-stabilizing section of the flow duct of the compact ventilation system and the at least one mechanical stabilizing section of the recoil membrane of the nonreturn valve can cooperate such that the recoil membrane is clamped in a defined manner between the at least one mechanical counter-stabilizing section of the flow duct and the at least one mechanical stabilizing section of the recoil membrane of the nonreturn valve. The at least one mechanical counter-stabilizing section of the flow duct may be, for example, a projection directed towards the longitudinal axis of the flow duct. Two projections directed towards the longitudinal axis of the flow duct and offset by 180° in relation to one another are preferably provided as mechanical counter-stabilizing sections. As an alternative, a web, which extends from an inner wall side of the flow duct to the opposite inner wall side of the flow duct, may be provided as a mechanical counter-stabilizing section in the flow duct of the compact ventilation system. The flow duct of the compact ventilation system is preferably formed by a flexible tube or tube element.

Further, provisions may be made in a preferred compact ventilation system for the volume flow meter to be arranged facing the second opening in the flow duct, for the nonreturn valve to be arranged facing the first opening in the flow duct and for the exhalation valve to be arranged between the volume flow meter and the nonreturn valve in the flow duct. Optimal flow of breathing air is guaranteed hereby during the phase of inhalation and optimal flow of exhaled air is guaranteed hereby during the phase of exhalation through the compact ventilation system. The exhalation valve preferably has a control line, which has a connection to the flow duct, with the flow duct in the area between the nonreturn valve and the fan. Breathing air can thereby be passed through the control line, so that the membrane or the exhalation opening of the exhalation valve is closed during the phase of inhalation based on the pressure within the control line, as a result of which an optimal flow of breathing air can be guaranteed through the nonreturn valve to the volume flow meter.

Provisions may especially preferably be made according to a variant of the present invention in a compact ventilation system for the volume flow meter to have a hot wire technology for carrying out a hot wire anemometry process. Highly accurate determination of the volume flow of breathing air or exhaled air within the flow duct of the compact ventilation system is guaranteed by a volume flow meter or flow sensor having such a configuration. The volume flow meter may be connected to an analysis unit via a data line. As an alternative to this, a radio module, especially an RFID module, may be integrated in the volume flow meter. Data measured by the volume flow meter can hereby be sent in a wireless manner to a remotely arranged analysis unit, so that optimal monitoring of the volume flow within the compact ventilation system can be ensured.

Further advantages, features and details of the present invention appear from the following description, in which exemplary embodiments of the present invention are described in detail with reference to the drawings. The features mentioned in the description may be essential for the present invention both individually in themselves or in any desired combination. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a schematic lateral view showing a first embodiment of a nonreturn valve for a compact ventilation system;

FIG. 6 is a schematic front view showing the nonreturn valve according to FIG. 5;

FIG. 7 is a schematic front view showing a recoil membrane of a nonreturn valve according to FIG. 5;

FIG. 10 is a schematic lateral view showing a third embodiment of a nonreturn valve according to the present invention for a compact ventilation system;

FIG. 11 is a schematic front view showing the nonreturn valve according to FIG. 10;

FIG. 12 is a schematic lateral view showing a fourth embodiment variant of a nonreturn valve according to the present invention for a compact ventilation system;

FIG. 13 is a schematic front view showing the nonreturn valve according to FIG. 12;

FIG. 14 is a schematic front view showing the nonreturn valve according to FIG. 12 in a slightly modified embodiment variant;

FIG. 15 is a schematic lateral view showing a fifth embodiment of a nonreturn valve according to the present invention for a compact ventilation system;

FIG. 16 is a schematic front view showing the nonreturn valve according to FIG. 15;

FIG. 17 is a schematic view showing a section through the recoil membrane of a nonreturn valve according to FIG. 15;

FIG. 20 is a schematic lateral view showing the mounting of the holding element including the recoil membrane on a tube element of a nonreturn valve;

FIG. 21 is a schematic lateral view showing the nonreturn valve shown in FIG. 20 at the end of the mounting;

DESCRIPTION OF PREFERRED EMBODIMENTS

Figure 1:
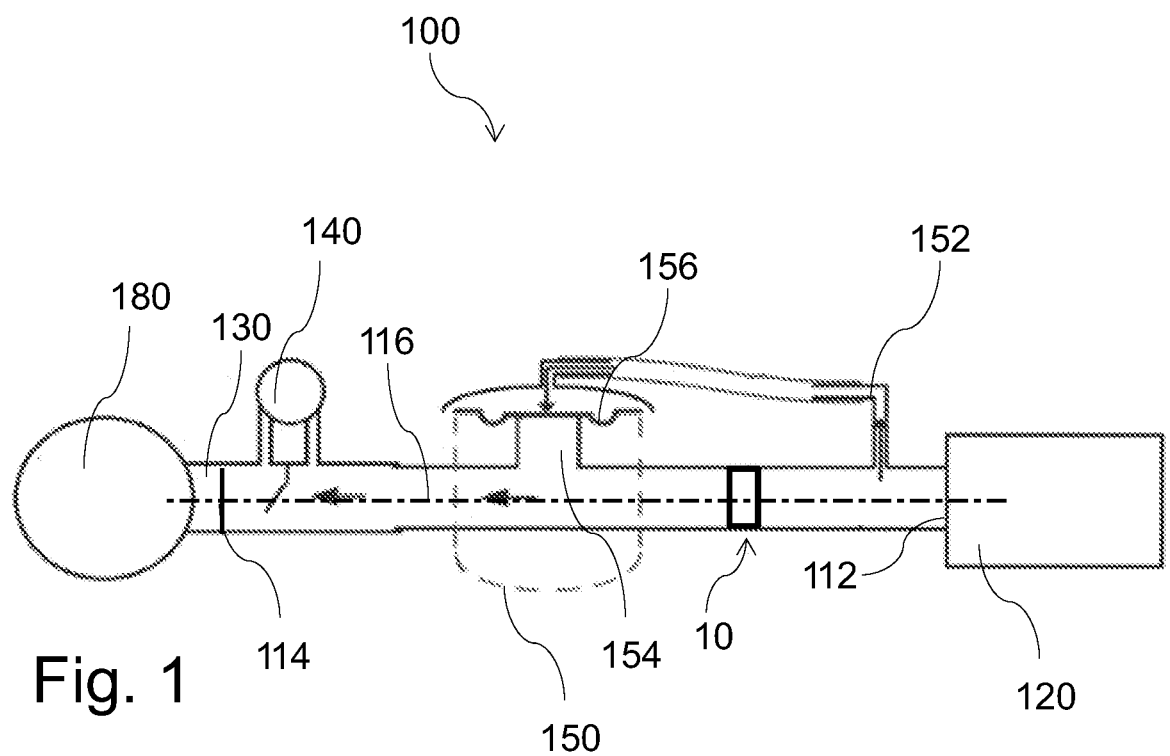
FIG. 1 is a schematic view showing a compact ventilation system according to the present invention during the phase of inhalation.

Referring to the drawings, elements having the same function and mode of operation are designated by the same reference numbers in FIGS. 1 through 23.

FIG. 1 schematically shows a compact ventilation system 100 according to the present invention. The compact ventilation system 100 has a fan 120, a tube 130 as well as a flow duct 110 for passing breathing air from the fan 120 through the flow duct 110 to the tube 130. The flow duct 110 has a second opening 114 for connecting the tube 130. The flow duct 110 further has a first opening 112 for connecting the fan 120. The compact ventilation system 100 further has a volume flow meter 140, which is arranged close to the tube 130 within the flow duct 110. Close means especially that the tube 130 is located at a distance of a few cm from the second opening 114 in the flow duct 110. A nonreturn valve 10 according to the present invention, shown only schematically here, is arranged close to the fan 120 within the flow duct 110. It is ensured hereby that breathing air provided by the fan 120 flows first through the nonreturn valve 10 before it is sent further through the flow duct 110 in the direction of the volume flow meter 140. An exhalation valve 150, which is closed during the phase of inhalation being shown here in order to guarantee the flow of the breathing air provided by the fan 120 to the volume flow meter 140 through the flow duct 110, is arranged between the nonreturn valve 10 and the volume flow meter 140. The compact ventilation system 100 or the exhalation valve 150 has a control line, which guarantees that some breathing air is branched off during the phase of inhalation before the flow through the nonreturn valve 10 and is fed to the exhalation valve 150, so that the membrane 156 of the exhalation valve 150 closes the exhalation opening 154 of the exhalation valve 150, so that breathing air provided by the fan 120 cannot escape from the exhalation valve 150 during the phase of inhalation. It is ensured hereby that the breathing air provided during the phase of inhalation can be fed in a defined manner to the volume flow meter 140 and hence to the patient 180.

Figure 2:
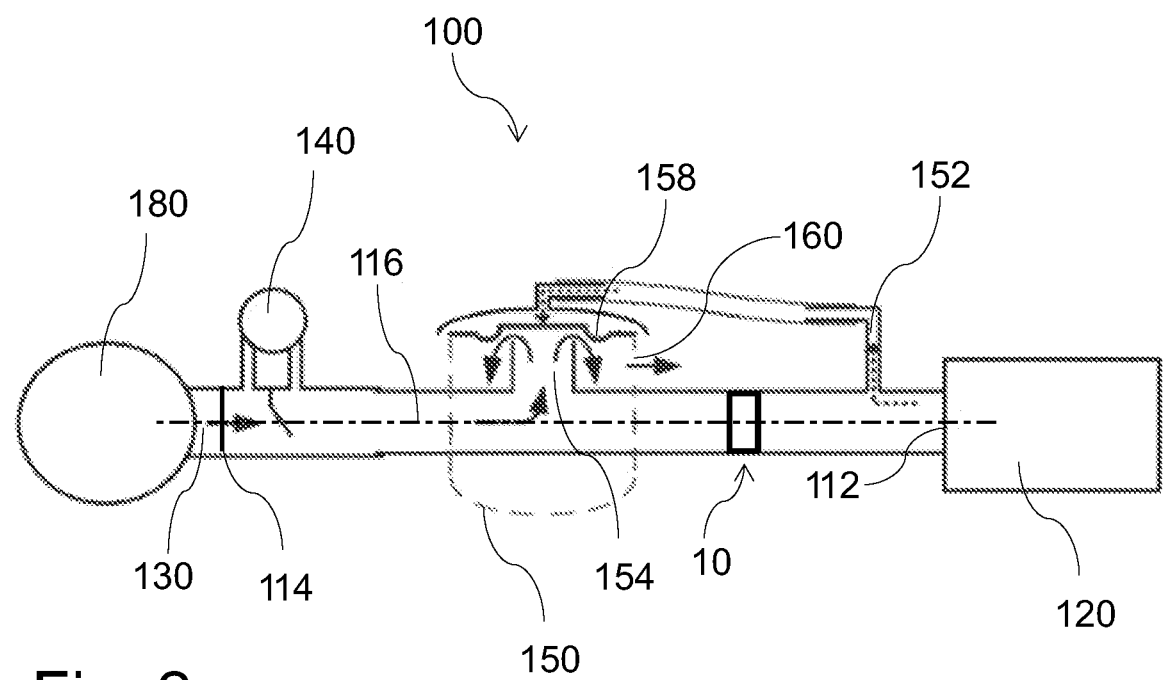
FIG. 2 is a schematic view showing the compact ventilation system according to FIG. 1 during the phase of exhalation.
Figure 3:
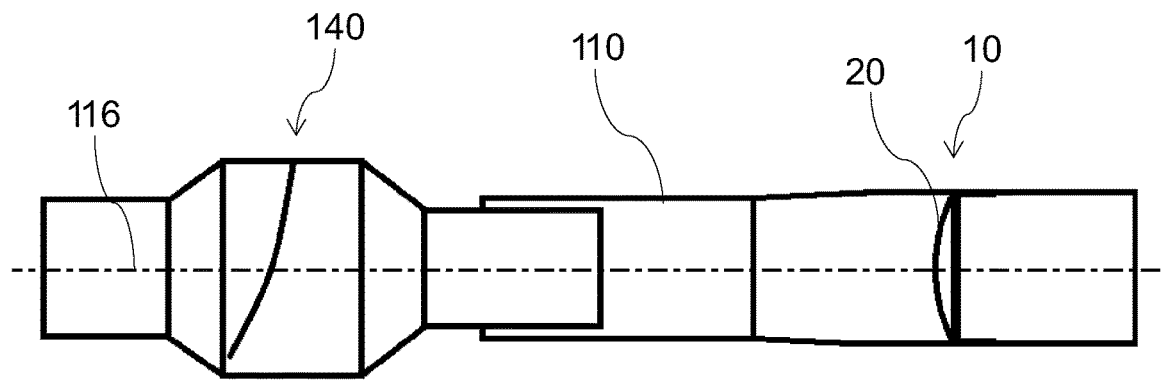
FIG. 3 is a schematic lateral view showing the flow of breathing air through a flow duct of a compact ventilation system.

FIG. 2 schematically shows the compact ventilation system 100 shown in FIG. 1 during the phase of exhalation. The air exhaled by the patient 180 flows through the tube 130, then through the volume flow meter 140, before it reaches the exhalation valve 150. The nonreturn valve 10 is closed by the arriving exhaled air, so that no exhaled air can be sent through this valve in the direction of the fan 120. The exhaled air presses the membrane 156 of the exhalation valve 150 into an open position 158, so that the exhalation opening 154 is released for drawing off exhaled air 160.

Figure 4:
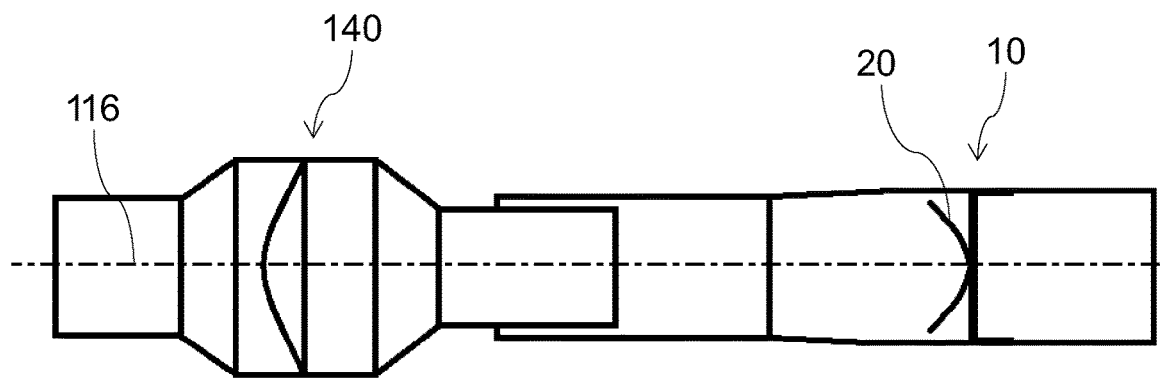
FIG. 4 is a schematic top view of the compact ventilation system, showing the flow through the flow duct of the compact ventilation system according to FIG. 3.

FIGS. 3 and 4 show each schematically a compact ventilation system 100, once in a lateral view, FIG. 3, and again in a top view, FIG. 4. The flow duct 110 is formed by a plurality of flow elements. A first flow element has the volume flow meter 140, and a second flow element, arranged at the first flow element, has the exhalation valve, not shown here, and the nonreturn valve 10. The recoil membrane 20 of the nonreturn valve 10 is in the phase of inhalation in both views. The recoil membrane 20 releases the flow of breathing air, which is provided by a fan 120, so that this can be sent in a defined manner through the nonreturn valve 10 and the flow duct 110 to the volume flow meter 140. The recoil membrane 20 always opens in the same, defined manner. This is guaranteed by the special configuration of the nonreturn valve 10.

FIG. 5 schematically shows a first embodiment of a nonreturn valve 10 according to the present invention. The nonreturn valve 10 has a recoil membrane 20, a holding element 40 as well as a tube element 70. The recoil membrane 20 has two mechanical stabilizing sections 22 in the form of segments 28, which cooperate with two mechanical counter-stabilizing sections 42, which are configured as counter-segments. The mechanical counter-stabilizing sections 42 are configured as hooks or projections projecting from the inner jacket surface of the tube element 70. The holding element 40 has counter-holding sections 46, which are used as counter-contact surfaces 56 for contacting the holding sections 26 of the recoil membrane 20, which said holding sections are configured as contact surfaces 36. In other words, the recoil membrane 20 is clamped in the area of its mechanical stabilizing sections 22 configured as segments between the mechanical counter-stabilizing sections 42 of the tube element 70 and the counter-holding sections 46 configured as counter-contact surfaces 56. The recoil membrane 20 is arranged as a result firmly in these areas within the nonreturn valve 10. A movement of these sections is not possible during the arrival of breathing air at the nonreturn valve 10. Only the two opening sections 24 of the recoil membrane 20 remain movable and can open in a defined manner on the arrival of waste air in order thus to guarantee a defined flow of the breathing air through the nonreturn valve 10. In a front view, FIG. 7 schematically shows a recoil membrane 20, as it is shown in FIG. 5. The two mechanical stabilizing sections 22 shown, which are configured as segments 28 of the recoil membrane 20, are clamped between the mechanical counter-stabilizing sections 42 of the tube element 70 and the counter-holding sections 46 or the counter-contact surface 56 of the holding element 40. Due to the mechanical stabilizing sections 22 being arranged on two opposite sides of the recoil membrane 20 and due to a holding section 26 configured as a suspension element 34 being provided in the area of the center 30 of the recoil membrane 20, it is ensured that when a flow of breathing air arrives from a fan 120 of a compact ventilation system 100, only the non-fastened opening sections 24, which extend between the two mechanical stabilizing sections 22 to the left and right of an imaginary straight line, can move.

In a front view, FIG. 6 schematically shows the nonreturn valve 10 according to FIG. 5. Two mechanical counter-stabilizing sections 42 and counter-segments 48, configured as projections and hooks, respectively, project from the tube element 70 of the nonreturn valve 10 in the direction of the longitudinal axis of the tube element 70. The recoil membrane 20 is locked behind these in the area of its mechanical stabilizing sections 22. The holding element 40 has in its bottom area a web, which extends from one side of the jacket surface 50 of the cylindrical holding element 40 to an opposite side of the jacket surface 50 of the cylindrical holding element 40. A counter-suspension element 54, which is configured as a recess and into which the holding section 26 configured as a suspension element 34 projecting from the recoil membrane 20 is passed in order to lock at the counter-suspension element 54, is present in this web. The recoil membrane 20 is held securely by this locking connection at the holding element 40 of the nonreturn valve 10. The breathing air provided by the fan 120 flows through the passages 58 of the holding element 40 and moves the opening sections 24 of the recoil membrane 20 in a defined, always the same manner, so that the further flow through the flow duct 110 of a compact ventilation system 100 can also take place in a defined manner. This in turn ensures that the flow arrives at a volume flow meter or a so-called flow sensor 140 in a controlled manner, so that the measurement accuracy of the volume flow meter 140 becomes predictable.

Figure 8:
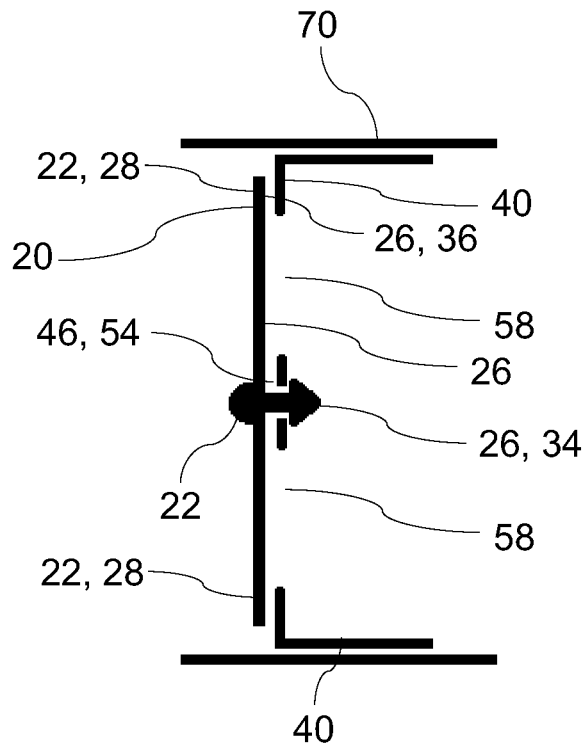
FIG. 8 is a schematic lateral view showing a second embodiment of a nonreturn valve for a compact ventilation system.
Figure 9:
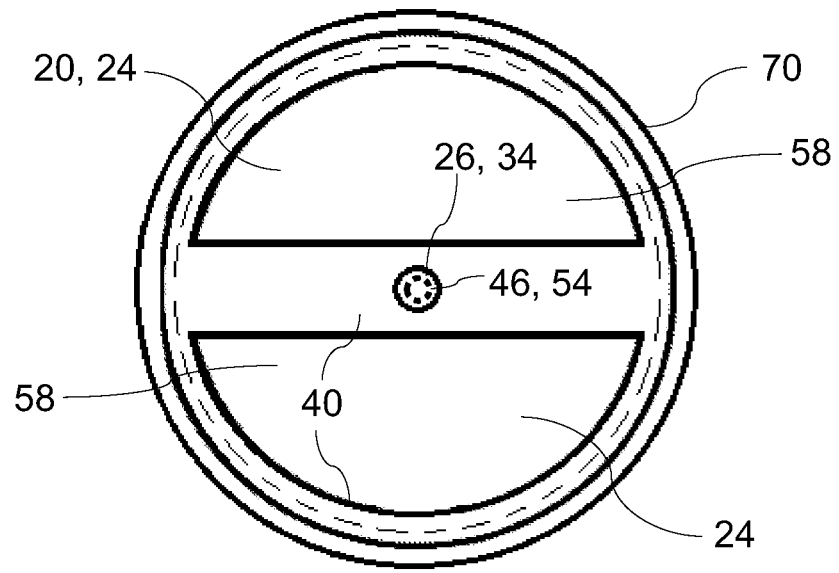
FIG. 9 is a schematic front view showing the nonreturn valve according to FIG. 8.

FIG. 8 schematically shows a second embodiment of a nonreturn valve 10 according to the present invention for a compact ventilation system 100. Contrary to the nonreturn valve 10 according to FIG. 5, the nonreturn valve 10 shown in FIG. 8 has no hooks or projections on the inner jacket surface 74 of the tube element 70. The mechanical stabilizing section 22 of the recoil membrane 20 is formed by a web-type thickening in the recoil membrane 20 itself This web-type thickening or reinforcing rib ensures that the recoil membrane 20 remains dimensionally stable in the area of the web-type thickening during a flow of breathing gas, i.e., the recoil membrane 20 retains its shape in this mechanical stabilizing section 22, so that only the opening sections 24 adjoining on the two sides of the mechanical stabilizing section 22 are movable here as well. In order for the recoil membrane 20 to be seated firmly at the holding element 40 of the nonreturn valve 10, the recoil membrane 20 has a holding section 26 configured as a suspension element 34. This suspension element 34 has a hammer-shaped or mushroom-shaped configuration and locks behind the counter-suspension element 54 of the counter-holding section 46 of the holding element 40, which said counter-suspension element is configured as a recess. A defined opening of the recoil membrane 20 can also be ensured by this special embodiment of the recoil membrane 20 of the nonreturn valve 10 during the flow of breathing gas, so that a permanently uniform flow to the volume flow meter 140 of a compact ventilation system 100 can be made available here as well.

The holding element 40 of this second embodiment of the nonreturn valve 10 has the same shape as the holding element 40 of the first embodiment of the nonreturn valve 10 according to FIG. 5. The counter-suspension element 54 configured as a recess is preferably provided centrally in the centrally extending web of the holding element 40.

FIG. 10 schematically shows a third embodiment variant of a nonreturn valve 10 according to the present invention for a compact ventilation system 100. The recoil membrane 20 is again suspended centrally at the holding element 40 here as well. The recoil membrane 20 has a suspension element 34, which has a hammer-shaped or mushroom-shaped configuration and which is locked behind the counter-suspension element 54 configured as a recess, which forms the counter-holding section 46 of the holding element 40. The recoil membrane 20 has again two mechanical stabilizing sections 22 configured as segments 28. These mechanical stabilizing sections 22 are clamped between the mechanical counter-stabilizing sections 42 of the holding element 40, which are configured as counter-segments 48, and the counter-holding sections 46 of the holding element 40, which are configured as counter-contact surfaces 46. For contacting the counter-contact surfaces 56, the recoil membrane 20 has corresponding contact surfaces 36. It is ensured by the locking of the mechanical stabilizing sections 22 of the recoil membrane 20 and by the contact of the holding sections 26 of the recoil membrane 20, which are configured as contact surfaces 36, with the counter-contact surface 56 of the holding element 40, that only the opening sections 24 of the recoil membrane 20 are movable and thus guarantee a defined flow of breathing air through the nonreturn valve 10.

FIG. 11 schematically shows the third embodiment variant of the nonreturn valve according to FIG. 10 in a front view.

FIG. 12 schematically shows a fourth embodiment of a nonreturn valve 10 according to the present invention for a compact ventilation system 100 in a lateral view. In this embodiment, the recoil membrane 20 has two suspension elements 32 having a hammer-shaped or mushroom-shaped configuration as mechanical stabilizing sections 22. These suspension elements 32 are plugged into two counter-suspension elements 52, which are configured as recesses and form the mechanical counter-stabilizing sections 42, so that they are locked at the holding element 40. In addition, another suspension element 34, which has a hammer-shaped or mushroom-shaped configuration and which holds the recoil membrane 20 centrally at a corresponding counter-suspension element 54 of the holding element 40, which said counter-suspension element is configured as a recess, is provided in the area of the center 30 of the recoil membrane 20. The suspension elements 32, 34 of the recoil membrane 20 extend on a straight line, so that the recoil membrane 20 is held along this straight line at the holding element 40 of the nonreturn valve 10 in a dimensionally stable manner. The recoil membrane 20 is moved in a defined manner during the flow of breathing air through the nonreturn valve 10 only in the area of the two opening sections 24, so that a uniform flow of breathing air is guaranteed through the nonreturn valve 10. A uniform, defined incoming flow can correspondingly also be guaranteed to a downstream volume flow meter 140 of a compact ventilation system 100 with such a nonreturn valve 10. Respective possible embodiment variants of the holding element 40 of the nonreturn valve 10 according to FIG. 12 are schematically shown in FIGS. 13 and 14. The holding element 40 may have a centrally extending web, see FIG. 13. As an alternative to this, the holding element 40 may have two webs extending in a cruciform pattern, see FIG. 14. These webs are used to receive the counter-suspension elements 52, 54 configured as recesses.

FIG. 15 schematically shows a fifth embodiment of a nonreturn valve 10 for a compact ventilation system 100. Contrary to the above embodiments of the nonreturn valves 10, this nonreturn valve 10 has no central suspension of the recoil membrane 20 at the holding element 40 of the nonreturn valve 10. In the area of the center 30 of the recoil membrane 20, the latter has a holding section 26 configured as a contact surface 36. It is ensured hereby that the recoil membrane 20 is held securely at the holding element 40 during the phase of exhalation. The recoil membrane 20 is otherwise held in its edge area at the holding element 40 only in the area of its mechanical stabilizing sections 22 and its holding section 26 configured as a contact surface 36. This means that the recoil membrane 20 is locked only at two edge areas at the holding element 40. It can be guaranteed hereby as well that only the opening sections 24 can be moved during the flow of breathing air in order thus to guarantee a defined flow of the breathing air through the nonreturn valve 10.

FIG. 17 schematically shows once again the recoil membrane 20 according to FIG. 15. FIG. 17 shows the recoil membrane 20 in a longitudinal section through its center 30, so that the opening sections 24 are not shown. The recoil membrane 20 has two mechanical stabilizing sections 22, which are configured as opposite segments 28. The recoil membrane 20 further has holding sections 26, which are configured as contact surfaces 36 and which are likewise used to come into contact with corresponding counter-holding sections 46 of the holding element 40, which are configured as counter-contact surfaces 56, in a positive-locking manner.

Figure 18:
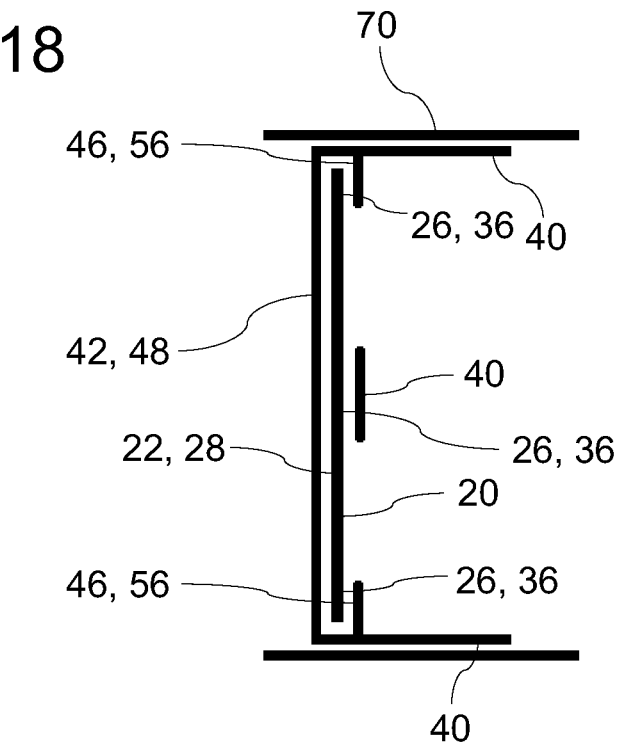
FIG. 18 is a schematic lateral view showing a sixth embodiment of a nonreturn valve according to the present invention for a compact ventilation system.
Figure 19:
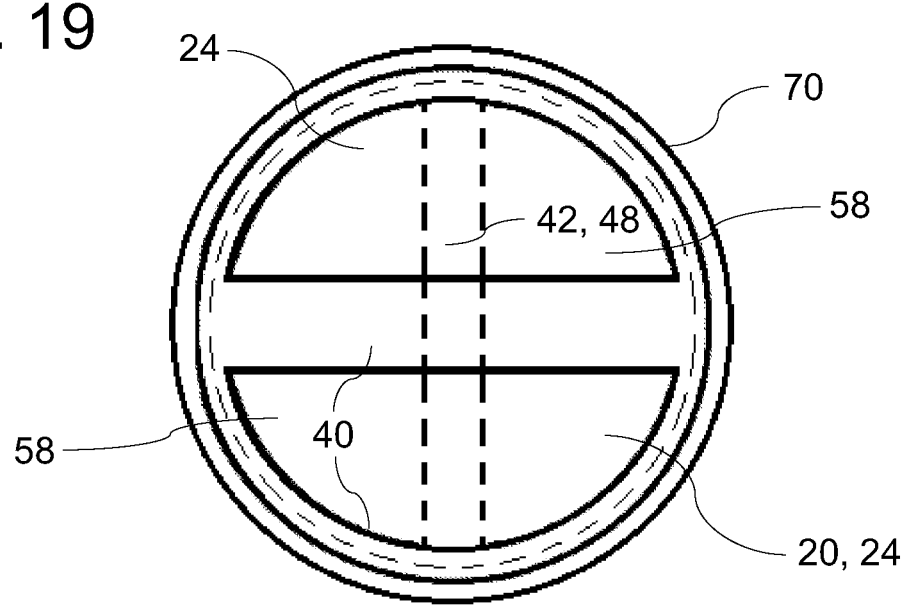
FIG. 19 is a schematic front view showing the nonreturn valve according to FIG. 18.

FIG. 18 schematically shows a sixth embodiment of a nonreturn valve 10 according to the present invention for a compact ventilation system 100 in a lateral view. Unlike in the nonreturn valve 10 according to FIG. 15, the holding element 40 of the nonreturn valve 10 does not have two mechanical counter-stabilizing sections 42 configured as projections or hooks, but a mechanical counter-stabilizing section 42 configured as a web. This mechanical counter-stabilizing section 42 configured as a web acts as a counter-segment 48 for the mechanical stabilizing section 22 of the recoil membrane 20, which stabilizing section is configured as a segment 28. This mechanical stabilizing section 22 of the recoil membrane 20 extends from one side of the recoil membrane 20 to an opposite, second side of the recoil membrane 20. The shape of the counter-segment 48 and of the mechanical counter-stabilizing section 42 of the holding element 40 is shown in FIG. 19 in a front view of the nonreturn valve 10.

The nonreturn valves 10 of the above-described six different embodiment variants, which are shown in front views, are always shown from the view of a fan 120 of a compact ventilation system 100, in which the nonreturn valves 10 are installed.

FIGS. 20 and 21 schematically show how a nonreturn valve 10, here in the example of the sixth embodiment of the nonreturn valve 10, is assembled. The tube element 70 of the nonreturn valve 10 has a sliding block guide 72 on its inner jacket surface 74. A projecting bolt 60 is provided on the outer jacket surface 62 of the holding element 40. The bolt 60 on the outer jacket surface 62 of the holding element 40 is inserted into the sliding block guide 72 of the tube element 70 and the holding element 40 is moved along the longitudinal axis of the tube element 70 until the holding element 40 has reached its defined position within the tube element 70. This defined position of the holding element 40 in the tube element 70 is shown schematically in FIG. 21. The bolt 60 is preferably locked in the defined position in a snap-in seat at the end of the sliding block guide 72 of the tube element 70, so that the holding element 40 is arranged firmly within the tube element 70.

Figure 22:
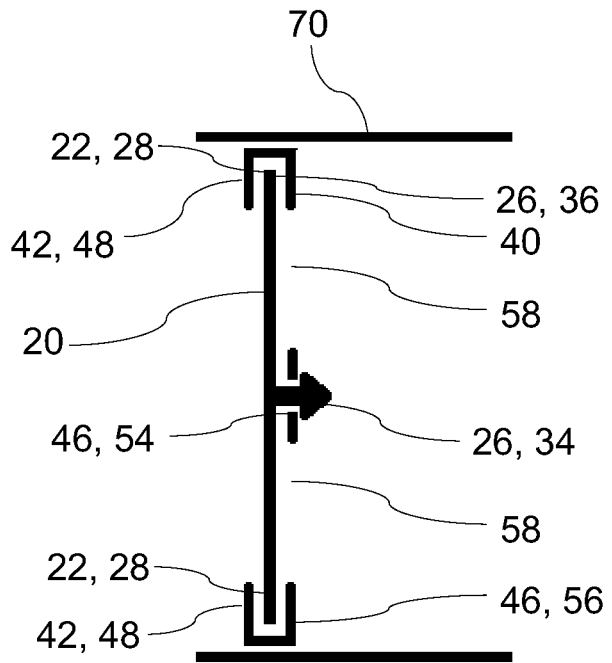
FIG. 22 is a schematic lateral view showing a seventh embodiment of a nonreturn valve according to the present invention for a compact ventilation system.

The holding element 40 is configured as a basket element in the above figures. This means that it has, on the one hand, a hollow cylindrical jacket surface 50, which has a ring element-shaped or disk-shaped bottom towards one end with corresponding passages 58. The holding element 40 according to FIG. 22 is likewise cylindrical, but is configured in the form of a disk or of a ring element. The functions of the nonreturn valve 10 otherwise correspond to those of the nonreturn valves 10 according to the above embodiments.

Figure 23:
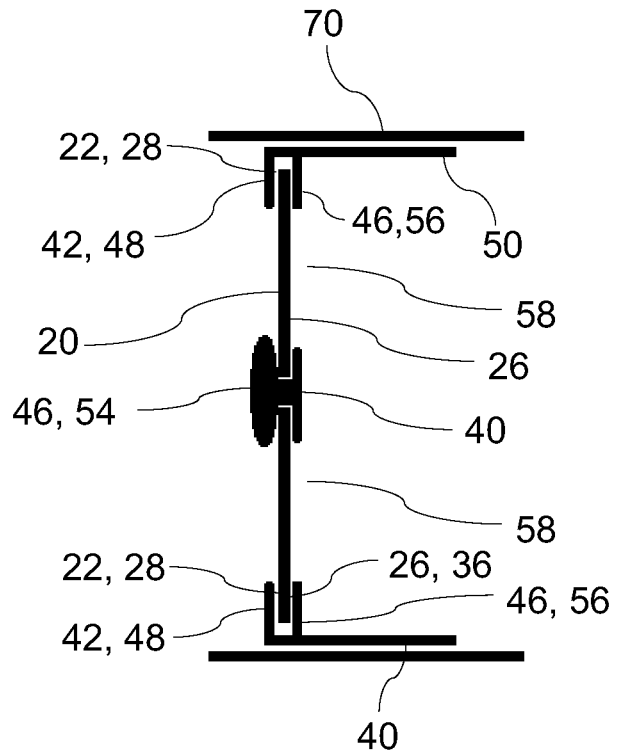
FIG. 23 is a schematic lateral view showing an eighth embodiment of a nonreturn valve according to the present invention for a compact ventilation system.

FIG. 23 schematically shows an eighth embodiment of a nonreturn valve 10 according to the present invention for a compact ventilation system 100. The counter-holding section 46 of the holding element 40 is a counter-suspension element 54, which projects from the holding element 40 and which is locked in a holding section 26 of the recoil membrane 20, which holding section is configured as a recess. The counter-suspension element 54 has here a width that is greater than the holding section 26 configured as a recess. In particular, the width of the counter-suspension element 54 is at least twice the width of the holding section 26 configured as a recess. The counter-suspension element 54 preferably has a radial extension in relation to the longitudinal axis of the holding section 26 configured as a recess, which extension corresponds to at least 2 to 3 times the diameter of the holding section 26 configured as a recess. A nonreturn valve 10 of such a configuration makes possible a defined retention of the recoil membrane 20 during an outflow of breathing air or during a flow of breathing air during the phase of inhalation. The counter-suspension element 54 preferably has an oblong shape, especially an oval-oblong shape. The counter-suspension element 54 locks the recoil membrane 20 at the holding element 40 and ensures that only the opening sections 24 of the recoil membrane 20, which are located to the left and right of the counter-suspension element 54, can be moved.

While specific embodiments of the invention have been shown and described in detail to illustrate the application of the principles of the invention, it will be understood that the invention may be embodied otherwise without departing from such principles.

APPENDIX:

LIST OF REFERENCE NUMBERS:

10 Nonreturn valve
20 Recoil membrane
22 Mechanical stabilizing section
24 Opening section
26 Holding section
28 Segment
30 Center of the recoil membrane
32 Suspension element
34 Suspension element
36 Contact surface
40 Holding element
42 Mechanical counter-stabilizing section
46 Counter-holding section
48 Counter-segment
50 Jacket surface
52 Counter-suspension element
54 Counter-suspension element
56 Counter-contact surface
58 Passages
60 Bolt
62 Outer jacket surface
70 Tube element
72 Sliding block guide
74 Inner jacket surface
100 Compact ventilation system
110 Flow duct
112 First opening
114 Second opening
116 Longitudinal axis
120 Fan
130 Tube
140 Volume flow meter
150 Exhalation valve
152 Control line
154 Exhalation opening
156 Membrane in closed position
158 Membrane in open position
160 Opening for drawing off exhaled air
180 Patient

What is claimed is:

1. A nonreturn valve for a compact ventilation system, the nonreturn valve comprising:
   a recoil membrane comprising at least one mechanical stabilizing section, at least one opening section and a holding section, the at least one mechanical stabilizing section comprising a mechanical stabilizing section circumferential peripheral edge surface;
   a holding element for holding the recoil membrane and for fastening the nonreturn valve on a flow duct of the compact ventilation system; and
   at least one mechanical counter-stabilizing section associated with the holding element or associated with the flow duct of the compact ventilation system, wherein:
   the mechanical stabilizing section circumferential peripheral edge surface is free of contact with the at least one mechanical counter-stabilizing section;
   the at least one mechanical stabilizing section cooperates with the at least one mechanical counter-stabilizing section;
   the at least one opening section provides a defined movement of the recoil membrane during an opening of the nonreturn valve; and
   the holding section holds the recoil membrane at a counter-holding section of the holding element.

2. A nonreturn valve in accordance with claim 1, wherein the holding element comprises a cylindrical, essentially disk-shaped, ring element-shaped configuration or comprises a basket element configuration with passages for flow of breathing air.

3. A nonreturn valve in accordance with claim 1, wherein:
   the mechanical stabilizing section comprises a segment of the recoil membrane or comprises two segments of the recoil membrane, which are located opposite each other in relation to a center of the recoil membrane; and
   the counter-stabilizing section comprises at least one counter-segment of the holding element or at least one counter-segment of the flow duct of the compact ventilation system; and
   the segment of the recoil membrane is in non-positive or positive-locking contact with the at least one counter-segment or the segments of the recoil membrane are in non-positive or positive-locking contact with the at least one counter-segment.

4. A nonreturn valve in accordance with claim 3, wherein the at least one counter-segment of the holding element is configured as a longitudinal web or as two hooks projecting radially from a jacket surface of the cylindrical holding element.

5. A nonreturn valve in accordance with claim 1, wherein:
   the mechanical stabilizing section comprises at least one suspension element projecting from the recoil membrane;
   the at least one suspension element is locked in at least one mechanical counter-suspension element of the holding element; and
   the counter-suspension element is configured as a recess.

6. A nonreturn valve in accordance with claim 1, wherein the mechanical stabilizing section comprises a web thickening of the recoil membrane.

7. A nonreturn valve in accordance with claim 1, wherein:
   the holding section of the recoil membrane comprises a suspension element, which projects from the recoil membrane and which locks into a counter-suspension element of the holding element and the counter-suspension element is configured as a recess; or
   the holding section of the recoil membrane comprises a contact surface on one side of the recoil membrane, which contact surface is configured for the clamping contact with the counter-holding section of the holding element, which counter-holding section of the holding element is configured as a counter-contact surface.

8. A nonreturn valve in accordance with claim 1, wherein the recoil membrane comprises two opening sections, which are arranged on two opposite sides of the recoil membrane in relation to the center of the recoil membrane.

9. A nonreturn valve in accordance with claim 1, further comprising a tube element, wherein the holding element is non-positive or positive-locking fastenable to an inner jacket surface of the tube element, the mechanical stabilizing section circumferential peripheral edge surface facing in a direction of the inner jacket surface of the tube element.

10. A nonreturn valve in accordance with claim 9, wherein:
a bolt is provided on an outer jacket surface of the holding element;
the tube element comprises a sliding block guide with an inner jacket surface, in which the bolt is lockable and guided.

11. A nonreturn valve in accordance with claim 1, wherein:
the counter-holding section of the holding element comprises a counter-suspension element, which projects from the holding element and which is locked into a holding section of the recoil membrane;
said holding section is configured as a recess; and
the counter-suspension element has a width that is greater than the holding section configured as a recess, and which has a size equaling at least twice a size of the holding section configured as a recess.

12. A compact ventilation system comprising:
a fan;
a tube;
a flow duct for passing through breathing air to a patient, wherein the flow duct comprises a first opening connecting to the fan, a second opening connecting to the tube, a volume, an exhalation valve and a nonreturn valve, the nonreturn valve comprising:
a recoil membrane comprising at least one mechanical stabilizing section, at least one opening section and a holding section, the at least one mechanical stabilizing section comprising a mechanical stabilizing section circumferential peripheral edge surface;
a holding element for holding the recoil membrane and for fastening the nonreturn valve on the flow duct; and
at least one mechanical counter-stabilizing section associated with the holding element or associated with the flow duct, wherein:
the at least one mechanical stabilizing section cooperates with the at least one mechanical counter-stabilizing section;
the mechanical stabilizing section circumferential peripheral edge surface is free of contact with the at least one mechanical counter-stabilizing section;
the at least one opening section provides a defined movement of the recoil membrane during an opening of the nonreturn valve; and
the holding section holds the recoil membrane at a counter-holding section of the holding element.

13. A compact ventilation system in accordance with claim 12, wherein the flow duct comprises the at least one mechanical counter-stabilizing section for cooperating with the at least one mechanical stabilizing section of the recoil membrane, wherein the mechanical stabilizing section circumferential peripheral edge surface never contacts the at least one mechanical counter-stabilizing section.

14. A compact ventilation system in accordance with claim 12, wherein the at least one mechanical counter-stabilizing section is a projection directed towards the longitudinal axis of the flow duct, the tube comprising an inner jacket surface, the mechanical stabilizing section circumferential peripheral edge surface facing in a direction of the inner jacket surface of the tube element.

15. A compact ventilation system in accordance with claim 12, further comprising a volume flow meter arranged facing the second opening in the flow duct, wherein the nonreturn valve is arranged facing the first opening in the flow duct, and the exhalation valve is arranged between the volume flow meter and the nonreturn valve in the flow duct.

16. A compact ventilation system in accordance with claim 15, wherein the volume flow meter comprises a hot wire configured to carry out a hot wire anemometry process.

17. A compact ventilation system in accordance with claim 12, wherein the holding element comprises a cylindrical, essentially disk-shaped, ring element-shaped configuration or comprises a basket element configuration with passages for flow of breathing air.

18. A compact ventilation system in accordance with claim 12, wherein:
the mechanical stabilizing section comprises a segment of the recoil membrane or comprises two segments of the recoil membrane, which are located opposite each other in relation to a center of the recoil membrane;
the counter-stabilizing section comprises at least one counter-segment of the holding element or at least one counter-segment of the flow duct of the compact ventilation system; and
the segment of the recoil membrane is in non-positive or positive-locking contact with the at least one counter-segment or the segments of the recoil membrane are in non-positive or positive-locking contact with the at least one counter-segment.

19. A compact ventilation system in accordance with claim 12, wherein:
the mechanical stabilizing section comprises at least one suspension element projecting from the recoil membrane;
the at least one suspension element is locked in at least one mechanical counter-suspension element of the holding element; and
the counter-suspension element is configured as a recess.

20. A compact ventilation system in accordance with claim 12, wherein:
the holding section of the recoil membrane comprises a suspension element, which projects from the recoil membrane and which locks into a counter-suspension element of the holding element and the counter-suspension element is configured as a recess; or
the holding section of the recoil membrane comprises a contact surface on one side of the recoil membrane, which contact surface is configured for the clamping contact with the counter-holding section of the holding element, which counter-holding section of the holding element is configured as a counter-contact surface.

* * * * *